(12) United States Patent
Harris et al.

(10) Patent No.: US 7,709,631 B2
(45) Date of Patent: May 4, 2010

(54) OXIDIZED MICROBIAL CELLULOSE AND USE THEREOF

(75) Inventors: Jeremy J. Harris, Furlong, PA (US); Gonzalo Serafica, Langhorne, PA (US); Christopher J. Damien, Newtown, PA (US); Heather R. Nonnenmann, Warminster, PA (US)

(73) Assignee: Xylos Corporation, Langhorne, PA (US)

( * ) Notice: Subject to any disclaimer, the term of this patent is extended or adjusted under 35 U.S.C. 154(b) by 231 days.

(21) Appl. No.: 11/700,241

(22) Filed: Jan. 31, 2007

(65) Prior Publication Data

US 2007/0213522 A1    Sep. 13, 2007

Related U.S. Application Data

(60) Provisional application No. 60/781,328, filed on Mar. 13, 2006.

(51) Int. Cl.
| C08B 16/00 | (2006.01) |
| C08B 1/00 | (2006.01) |
| A61K 31/727 | (2006.01) |
| A61F 2/00 | (2006.01) |
| A61F 2/02 | (2006.01) |

(52) U.S. Cl. .............................. 536/57; 536/56; 514/57; 424/424; 623/11.11

(58) Field of Classification Search .................. 536/57, 536/56; 514/57; 424/424; 623/11.11
See application file for complete search history.

(56) References Cited

U.S. PATENT DOCUMENTS

| 3,630,194 A | 12/1971 | Boardman |
| 3,872,862 A | 3/1975 | Hume |
| 4,588,400 A | 5/1986 | Ring et al. |
| 4,643,181 A | 2/1987 | Brown |
| 4,650,674 A | 3/1987 | Aggarwal et al. |
| 4,655,756 A | 4/1987 | Fawkes |
| 4,655,758 A | 4/1987 | Ring et al. |
| 4,767,402 A | 8/1988 | Kost et al. |
| 4,788,146 A | 11/1988 | Ring et al. |
| 4,836,884 A | 6/1989 | McAuslan |
| 4,837,079 A | 6/1989 | Quantrille et al. |
| 4,912,049 A | 3/1990 | Farah |
| 4,942,128 A | 7/1990 | Brown, Jr. |
| 4,946,377 A | 8/1990 | Kovach |
| 5,019,034 A | 5/1991 | Weaver et al. |
| 5,073,373 A | 12/1991 | O'Leary et al. |
| 5,180,398 A | 1/1993 | Boardman et al. |
| 5,224,927 A | 7/1993 | Tapper |
| 5,290,558 A | 3/1994 | O'Leary et al. |
| 5,308,625 A | 5/1994 | Wong et al. |
| 5,433,996 A | 7/1995 | Kranzler et al. |
| 5,441,508 A | 8/1995 | Gazielly et al. |
| 5,510,396 A | 4/1996 | Prewett et al. |
| 5,540,669 A | 7/1996 | Sage, Jr. et al. |
| 5,558,861 A | 9/1996 | Yamanaka et al. |
| 5,580,348 A | 12/1996 | Blaney et al. |
| 5,662,924 A | 9/1997 | Rhodes |
| 5,702,409 A | 12/1997 | Rayburn et al. |
| 5,718,973 A | 2/1998 | Lewis et al. |
| 5,810,855 A | 9/1998 | Rayburn et al. |
| 5,830,493 A | 11/1998 | Yokota et al. |
| 5,846,213 A | 12/1998 | Wan |
| 5,942,218 A | 8/1999 | Kirschner et al. |
| 6,008,254 A | 12/1999 | Kligman et al. |
| 6,030,635 A | 2/2000 | Gertzman et al. |
| 6,031,148 A | 2/2000 | Hayes et al. |
| 6,071,727 A | 6/2000 | Bungay et al. |
| 6,156,056 A | 12/2000 | Kearns et al. |
| 6,156,334 A | 12/2000 | Meyer-Ingold et al. |
| 6,179,872 B1 | 1/2001 | Bell et al. |
| 6,206,931 B1 | 3/2001 | Cook et al. |
| 6,238,691 B1 | 5/2001 | Huang |
| 6,245,081 B1 | 6/2001 | Bowman et al. |
| 6,299,902 B1 | 10/2001 | Jun et al. |
| 6,320,093 B1 | 11/2001 | Augustine et al. |
| 6,369,289 B1 | 4/2002 | Orr, III |
| 6,487,447 B1 | 11/2002 | Weimann et al. |
| 6,599,518 B2 | 7/2003 | Oster et al. |
| 6,620,166 B1 | 9/2003 | Wenstrom, Jr. et al. |
| 6,635,755 B1 | 10/2003 | Jaschinski et al. |
| 6,673,363 B2 | 1/2004 | Luo et al. |

(Continued)

FOREIGN PATENT DOCUMENTS

WO    WO 03/020191 A1    3/2003

(Continued)

OTHER PUBLICATIONS

Shenai, V.A., Wagh, S.P. (1974) Studies in chemically Modified Celluloses. VII. Periodate Oxidation of Cellulose Dyed with Reactive Dyes. Journal of Applied Polymer Science, vol. 18, p. 2917-2926.*

(Continued)

Primary Examiner—Shaojia Anna Jiang
Assistant Examiner—Scarlett Goon
(74) Attorney, Agent, or Firm—Foley & Lardner LLP

(57) ABSTRACT

This application describes a bioresorbable biocellulose suitable for medical and surgical applications. In particular, the invention describes periodate oxidized microbial cellulose that can be produced to have any mechanical and degradation profile, depending on the desired application of the oxidized cellulose.

19 Claims, 5 Drawing Sheets

U.S. PATENT DOCUMENTS

| | | | |
|---|---|---|---|
| 6,706,279 | B1 | 3/2004 | Hazzi |
| 6,755,863 | B2 | 6/2004 | Ferree |
| 6,800,753 | B2 | 10/2004 | Kumar |
| 6,814,741 | B2 | 11/2004 | Bowman et al. |
| 6,852,330 | B2 | 2/2005 | Bowman et al. |
| 6,867,247 | B2 | 3/2005 | Williams et al. |
| 6,946,003 | B1 | 9/2005 | Wolowacz et al. |
| 2002/0107223 | A1 | 8/2002 | Oster et al. |
| 2003/0203012 | A1 | 10/2003 | Serafica et al. |
| 2004/0040096 | A1 | 3/2004 | Saferstein et al. |
| 2004/0096509 | A1 | 5/2004 | Hutchens et al. |
| 2004/0224023 | A1 | 11/2004 | Hunter et al. |

FOREIGN PATENT DOCUMENTS

| | | |
|---|---|---|
| WO | WO 2005/003366 A1 | 1/2005 |
| WO | WO 2006/017729 A2 | 2/2006 |

OTHER PUBLICATIONS

Lazarus et al., "Definitions and Guidelines for Assessment of Wounds and Evaluation of Healing," *Arch. Dermatol.*, 1994, pp. 489-493; vol. 130.

Kabara (Ed.) *Cosmetic and Drug Preservation: Principles and Practice*, Marcel Dekker, Inc., New York and Basel, 1994, pp. 728-730.

Schramm et al., "Factors affecting Production of Cellulose at the Air/Liquid Interface of a Culture of *Acetobacter sylinum*," *J. Gen. Microbiol.*, 1954, pp. 123-129, vol. 11.

Fontana et al., "*Acetobacter* Cellulose Pellicle as a Temporary Skin Substitute," *Applied Biochemestry and Biotechnology*, 1990, pp. 253-264, vol. 24/25.

Dimitrijevich, S. D., et al., "Biodegradation of Oxidized regenerated Cellulose," *Carbohydrate Research*, V. 195, 247-256 (1990).

Dimitrijevich, S. D., et al., "In vivo degradation of oxidized regenerated cellulose," *Carbohydrate Research*, V. 198, 331-341 (1990).

Martson, M., et al., "Biocompatibility of Cellulose Sponge with Bone," *Eur. Surg. Res.*, V. 30, 426-432 (1998).

Martson, M., et al., "Connective Tissue Formation in Subcutaneous Cellulose Sponge Implants in the Rat," *Eur. Surg. Res.*, V. 30, 419-425 (1998).

Mello, L. R., et al., "Duraplasty with Biosynthetic Cellulose: An Experimental Study," *Journal of Neurosurgery*, V. 86, 143-150 (1997).

Miyamoto, T. et al., "Tissue biocompatibility of cellulose and its derivatives," *J. Biomed. Mat. Res.*, V. 23, 125-133 (1989).

Pajulo, O. et al., "Viscose cellulose sponge as an implantable matrix: Changes in the structure increase production of granulation tissue," *J. Biomed. Mat. Res.*, V. 32, 439-446 (1996).

Brown-Etris et al., "Evaluation of a Biosynthetic Material: A New Wound Dressing Concept," Abstract, 1 Sheet, presented as a poster around Apr. 1998.

Redacted agreement, Exhibit A to Rule 132 Declaration of Russell Hoon.

Jun. 22, 1998 510(k) approval No. K974251 for X-Cell Wound Dressing (printed out from FDA web site).

Chiarello, Kaylynn, "Breaking the Barrier: Advances in Transdermal Technology," Pharmaceutical Technology, Oct. 2004, pp. 46-56.

Krystynowicz et al., "The evaluation of usefulness of microbial cellulose as a wound dressing material," Med. Fac. Landbouw. Univ. Gent, 65/3a, 2000, pp. 213-220.

Koh J.L., et al., "Supplementation of Rotator Cuff Repair with a Bioresorbable Scaffold," *Am. J. Sports Med.* 30:410-413, 2002.

Martson, M., et al., "Is Cellulose sponge degradable or stable as an implantation material? An in vivo subcutaneous study in the rat," *Biomaterials*, V. 20, 1989-1995 (1999).

"Some of These Companies Forecast Revenues of More Than $25 Million," May/Jun. 1999, 1 Sheet, Your Company, p. 48-49 .

* cited by examiner

OXIDIZED MICROBIAL CELLULOSE AND USE THEREOF

CROSS-REFERENCE TO RELATED APPLICATIONS

This application claims benefit of U.S. Provisional Application Ser. No. 60/781,328, filed Mar. 13, 2006, the entire contents of which are incorporated by reference herein.

BACKGROUND

1. Field of Invention

This invention relates to oxidized polysaccharide materials suitable for medical and surgical applications. In particular, the invention describes periodate oxidized microbial cellulose that is produced to have a specific mechanical and degradation profile, depending on the desired application of the oxidized cellulose.

The invention also relates to the use of the periodate oxidized microbial cellulose as a bioresorbable matrix for human tissue substitutes, closure reinforcement, suture buttressing, guided tissue regeneration, musculoskeletal applications, active agent delivery and tissue engineering scaffolds.

2. Background of the Invention

Oxidized cellulose has long been manufactured for use medically as haemostatic agents (e.g., SURGICEL™, Ethicon, Somerville, N.J. and Oxycell™, Becton-Dickinson, Morris Plains, N.J.) and as a barrier material to prevent adhesions following surgery (e.g., INTERCEED™, Ethicon, Somerville, N.J.). The key feature of oxidized cellulose is that it is absorbable when implanted in the body, whereas non-oxidized cellulose is not. The proposed mechanism of resorption of oxidized cellulose is by hydrolytic cleavage of the polymer into smaller oligosaccharides which are further metabolized and eliminated by the body. Complete absorption of such materials can be substantially achieved in two weeks to three months after implantation.

Most oxidized cellulose that is commercially available is plant-derived or synthetically regenerated to fabricate the resulting medical device. The material is first processed to the desired physical form and is then woven or knitted into a fabric prior to exposure to an oxidizing agent. Dinitrogen tetroxide is believed to be the only oxidizing agent currently being used to produce oxidized cellulose medical products. The use of other oxidation agents has been suggested, however, but to date, there have been no reports of commercially available oxidized cellulose medical devices created by other means besides the dinitrogen tetroxide oxidation process. Thus, the vast majority of clinical data on oxidized cellulose comprises non-microbial forms of cellulose oxidized by dinitrogen tetroxide.

Although other oxidation procedures have been developed to create bioresorbable cellulose, such processes do not describe using cellulose from microbial sources. For example, Kumar (U.S. Pat. No. 6,800,753) discloses sodium meta-periodate as an oxidizing agent for regenerated cellulose. Furthermore, Singh discloses the use of sodium meta-periodate for oxidation of cellulose, but only describes a powdered form of cellulose from a non-microbial source.

Combining Kumar and Singh, it is not evident that the use of microbial cellulose as a starting material for periodate oxidized cellulose would result in a mechanically functional material. In fact, Kumar specifically discourages the use of cellulose from microbial sources because of the lack of plasticity of microbial cellulose and the loss of the higher ordered structure of microbial cellulose during the solvent dissolving step. And it is not apparent from Singh that microbial cellulose would be suitable because of the crystalline and laminar structure of microbial cellulose. In fact, the current inventors were unexpectedly able to oxidize microbial cellulose and maintain mechanical strength while producing a biodegradable material.

In addition, neither Kumar nor Singh describe the use of supporting electrolytes during the periodate oxidation process or the utilization of differing drying techniques to confer different mechanical and degradation properties on the oxidized cellulose. Likewise, Jaschinski et al. (U.S. Pat. No. 6,635,755) describe a polysaccharide oxidation process with periodate in conjunction with TEMPO to create a material with oxidation occurring at all three alcoholic sites of the anhydroglucose repeat unit. Jaschinski et al., however, does not describe microbial cellulose as a suitable polysaccharide material and do not rely on the specific oxidative nature of periodate in conjunction with a supporting electrolyte.

Furthermore, Kim et al. describe periodate oxidation of plant cellulose obtained from marine alga. The oxidation process consists of the oxidation of cellulose microfibrils at a ratio of 10.7 mol $NaIO_4$ for 1 mol of glucopyranose for the desired reaction time. Again there is no description of the use of a supporting electrolyte during the oxidation process or a specific drying technique. Kim concludes that it is very important to choose the proper starting material to control the oxidation process, thus demonstrating that not all cellulose reacts the same when oxidized with periodate.

Ring et al. (U.S. Pat. Nos. 4,588,400, 4,655,758, and 4,788,146), however, does disclose the use of microbial cellulose for topical medical applications but does not describe oxidizing such films to produce a bioresorbable oxidized microbial cellulose for use as implantable medical devices or tissue engineering matrices. And Hutchens et al. (U.S. Patent Application No. 20040096509) also describe microbial cellulose but do not teach a bioresorbable version of the cellulose.

There is a need in the art for oxidized microbial cellulose that can have a given mechanical and degradation profile to fit a number of medical and surgical applications. Indeed, the use of microbial cellulose allows the creation of oxidized cellulose films which are able to maintain a high degree of laminar structure and crystallinity as opposed to amorphous oxidized regenerated cellulose. The non-woven laminar structure of microbial cellulose allows the material to maintain mechanical strength and at the same time be rendered bioresorbable.

SUMMARY OF THE INVENTION

It is an object of the invention to provide a new resorbable form of microbial cellulose that may be used for a wide variety of medical and surgical applications. Another objective is to provide resorbable microbial cellulose having desirable physical and chemical properties for uses as a resorbable matrix for human tissue substitutes, closure reinforcement, suture buttressing, guided tissue regeneration, musculoskeletal applications, active agent delivery and tissue engineering scaffolds. The microbial cellulose is oxidized, and the desired degree of oxidation is achieved by varying a factor such as oxidizing agent concentration, oxidizing agent solution volume, oxidizing agent:cellulose ratio, supporting electrolyte concentration, pre-soak in supporting electrolyte solution, reaction temperature, reaction duration, or a combination thereof.

Also provided in the invention is a method of producing oxidized microbial cellulose that can be specifically produced to have certain mechanical and degradation properties, depending on the application of the cellulose. The method comprises (i) producing microbial cellulose and (ii) oxidizing the microbial cellulose with a solution of periodate, such as sodium meta periodate. The oxidation process may be done with or without the use of a supporting electrolyte, and drying the oxidized microbial cellulose can be with a drying technique such as air drying, oven drying, supercritical $CO_2$ drying, or solvent dehydration, or a combination thereof. The method also optionally comprises a pre-soaking process, with or without a supporting electrolyte, prior to oxidation.

Still another objective is to provide a novel method or production process for the preparation of these aforementioned materials that will yield the desirable properties for each particular product application.

Also described herein is a method for making a bioresorbable medical material comprising (i) producing microbial cellulose and (ii) oxidizing the microbial cellulose with a solution of sodium meta-periodate. In one embodiment, the bioresorbable medical material is a suture, hemostat, wound covering, implantable tissue substitute, tissue engineering matrix, or an adhesion prevention device. The medical material can be used for repair and/or regeneration of a musculoskeletal tissue, a neurological tissue, such as the dura,; cardiovascular tissue, abdominal tissue, bladder neck suspension, gastroplasty, hernia repair, gastrointestinal closure, guided tissue regeneration for a dental application, or a bulking agent for plastic or reconstructive surgery, for example.

DETAILED DESCRIPTION OF THE INVENTION

Figure 1:
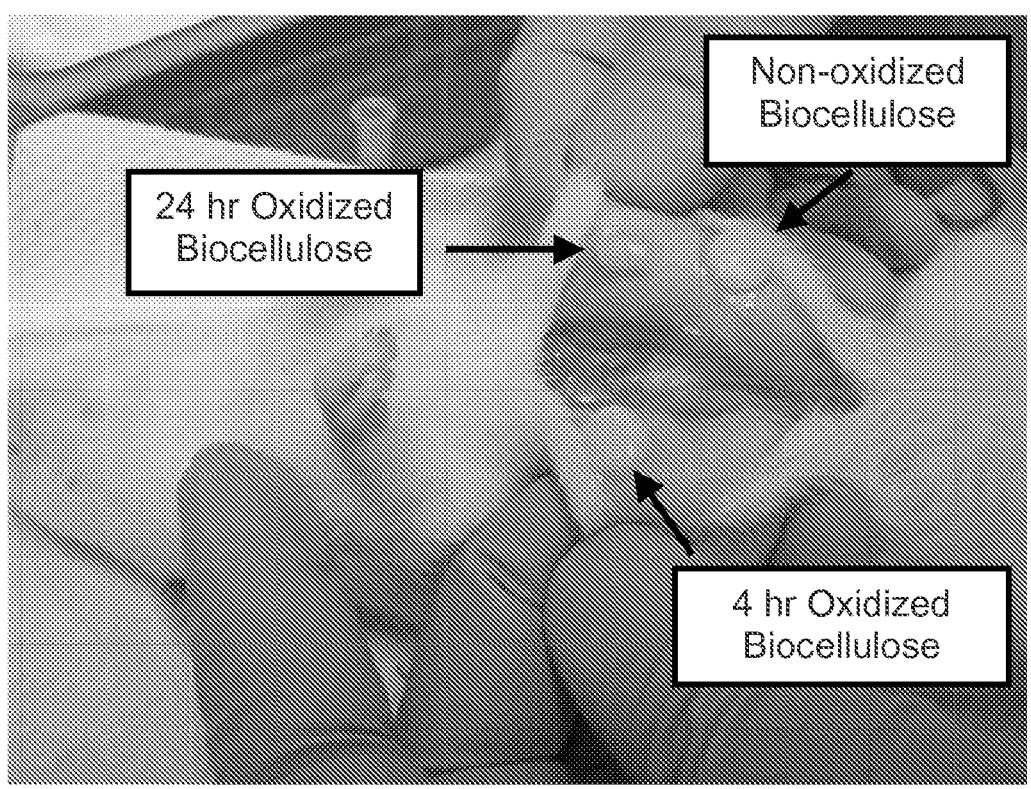
FIG. 1: Gross observation of oxidized microbial cellulose explants at 4 weeks.

Unless otherwise specified, all occurrences of "a," "an," or "the" mean at least one.

The terms "bioresorbed", "bioresorbable", "bioresorption" and permutations thereof refer to a substance that is naturally eliminated or degraded following topical or internal application of the substance to a mammal.

Oxidized Microbial Cellulose

In one embodiment, the present invention comprises oxidized microbial cellulose. In one embodiment, the microbial cellulose can be obtained from *Acetobacter, Rhizobium, Agrobacterium, Pseudomonas,* or *Sphaerotilus*. But preferably, the microbial cellulose is obtained from *Acetobacter xylinum*. The process of obtaining microbial cellulose can be done by techniques known in the art. See, for example, U.S. Pat. No. 6,599,518, which is incorporated herein by reference in its entirety.

In another embodiment, the addition of a supporting electrolyte prior to and/or during the oxidation process produces an oxidized material that maintains its original mechanical properties while rendering the material bioresorbable. In addition, a final drying step is utilized to provide an additional means to control both the mechanical and degradation properties of the oxidized biocellulose. The final level of oxidation for the microbial cellulose can be tailored to the specific product application, but preferably, the level of oxidation is sufficient to render the microbial cellulose bioresorbable at a desired rate of degradation including rates ranging from as little as one day to over one year. In other words, the oxidized microbial cellulose can be prepared so as to be resorbable in about one, two, three, four, or five days, about one, two, or three weeks, about one, two, three, four, five, six, seven, eight, nine, ten, or eleven months, or about one or two years.

The oxidized microbial cellulose of the invention or composites containing oxidized microbial cellulose can be used in a variety of forms, including a pad, pellicle, strip, suture, film, fluid, suspension, putty, paste, and gel. But preferably, the oxidized microbial cellulose is in the form of a pellicle or pad with a multi-laminar cross section or a putty/paste consistency for packing and filling defects. Other forms can be envisioned depending on the requirements of the biomaterial.

The oxidized microbial cellulose of the present invention is useful in a variety of medical applications, including wound dressings or bioresorbable matrices for human tissue substitutes, tissue closure reinforcement, suture buttressing, guided tissue regeneration, musculoskeletal applications, active agent delivery and tissue engineering scaffolds. In particular, the oxidized microbial cellulose of the invention can be used as a bioresorbable hemostatic agent to control bleeding, a wound dressing, an implantable adhesion barrier or anti-adhesion device for use in surgery, an implantable bulking agent instead of collagen for various types of surgeries including urological and aesthetic applications, a carrier for a biologically active agent or drug to form an implantable drug delivery device or prolonged delivery system, a gel formed with a physiologically-acceptable liquid, a gel or liquid for ophthalmic solutions and applications, a gel or fluid for skin augmentation and other cosmetic applications, bone filler, fitted sheath, implant for restoration of skeletal defects and other bone applications, tissue substitute, a surgical augmentation device such as bladder neck suspension sling, a fitted sheath for articulation of various types of prostheses such as hip and knee, a ligament or tendon scaffold for new tissue formation, a breast implant or breast reconstructive device, among others.

The oxidized microbial cellulose described herein is believed to sustain growth and proliferation of both epidermal cells and dermal cells leading to the formation of an intact biologically-active skin. Also, it is believed to support growth of cartilage-derived chondrocytes for the fabrication of cartilage tissue and endothelial cell growth, and prevent platelet and smooth muscle adhesion for use as a vascular graft. It is also believed to support growth of nerve-derived Schwann cells while delivering growth factors used for nerve regeneration, support corneal epithelial cell proliferation, and support adhesion and permeation for nutrient and fluid transport. It may also be used to form an artificial cornea and support mesenchymal cell proliferation that can lead to a variety of tissue structures depending on the area of implantation.

Additionally, the oxidized microbial cellulose of the invention can be used in combination with other materials such as polymers, collagen, proteins, peptides, cells, other forms of cellulose and biologically active agents to enhance its efficacy for a particular application. For example, the oxidized microbial cellulose described herein can also be mixed with various biomaterials, such as tricalcium phosphate, dicalcium phosphate, hydroxyapatite, resorbable and non-resorbable biopolymers, including collagen, polylactic acid, polyglycolic acid, poly ε-caprolactone, etc. to form composites. Other materials such as humectants and polyols such as glycerin and polyethylene glycol may be incorporated to adjust the physical and drying properties of the oxidized microbial cellulose. Additionally, active agents such as Bone Morphogenetic Proteins (BMP), platelet derived growth factors (PDGF), transforming growth factors (TGF), growth and differentiation factors (GDF), insulin-like growth factor (IGF), epidermal growth factor (EGF), demineralized bone matrix (DBM), Factor VIII and the like can be added to the microbial cellulose or composites. Likewise viable differentiated and undifferentiated cells for growth of bone, cartilage, skin, vessels, organs, etc. can be mixed with the oxidized microbial cellulose.

Method of Making

Also described herein is a method of making oxidized microbial cellulose comprising (i) harvesting microbial cellulose pellicles from a bacteria, such as *Acetobacter xylinum*, and (ii) oxidizing the microbial cellulose with a solution comprising sodium periodate and optionally, a salt, such as a salt from alkali metals, transition metals, and polyelectrolytes. Preferably, the salt is NaCl. The salt contributes to more uniform oxidation. In one embodiment, the method further comprises a dehydration step. As described below, the dehydration step may be air-drying, solvent drying (by, for example, a water-miscible solvent such as methanol, ethanol, propanol, isopropanol, acetone, tetrahydrofuran, butanol, 2-butanol, glycerol, or mixtures thereof, followed by air-drying, oven drying, or supercritical $CO_2$ drying.

As described herein, microbial cellulose can be obtained by inoculating sterilized media with bacteria, such as *A. xylinum*. The inoculated media is then used to fill bioreactor trays to a fixed volume, for example, 50, 110, 220, 330, 360, and 440 g, which are then incubated until the desired cellulose content is achieved, about 4 days (50 g-samples) to 21 days (440 g samples).

Following cellulose harvesting, the microbial cellulose pellicle is chemically treated to remove most of the non-cellulose material, including rendering the cellulose non-pyrogenic. All processing/shaping occurs after the cellulose is grown. The material can either be shaped before oxidation or after, depending on the final desired properties. The pad can be cleaned with sodium hydroxide, for example, to destroy the pyrogens but other cleaning techniques are known in the art. The pad may also be bleached with a solution such as hydrogen peroxide and water, typically in the range of 0.25% to about 3% hydrogen peroxide.

The pellicle is then soaked in an aqueous solution, optionally with a supporting electrolyte for about 30 minutes up to about 24 hours, followed by treatment with an oxidizing agent soaking solution, preferably sodium meta-periodate and optionally containing a supporting electrolyte. The electrolyte solution can be a 0.001-1M salt solution, preferably a 0.1-0.5M NaCl solution.

The oxidizing agent concentration and reaction volume are chosen to provide the desired periodate to cellulose ratio to yield oxidized microbial cellulose with the desired degree of oxidation. Excess oxidizing agent is then removed and the material is fabricated into its final form by final processing, addition of desired active agents, packaging, and sterilization.

The concentration of the oxidizing agent, reaction temperature, periodate to cellulose ratio, and reaction time can be varied to produce different levels of oxidation depending on the desired physical and chemical properties of the microbial cellulose. For example, the molarity of oxidizing agent can be in the range of 0.005M to 0.5M, the temperature can be from about 5 to 50° C. (i.e., 5 to 50° C., +/−5° C.), and the periodate to cellulose ratio can be 0.1-10. Preferably, the microbial cellulose can be oxidized for at least 30 minutes, or 1, 6, 12, or 24 hours, at least 1 day, or at least 2 days or longer. Thus, variable oxidation also affects the rate of degradation of the material allowing for increased rate of resorption at higher levels of oxidation.

In another preferred embodiment of the method of making oxidized microbial cellulose, after depyrogenation the oxidized microbial cellulose is cross-linked, either by chemical means using polyamines, such as polyethylenamine, polyalcohols, such as polyvinyl alcohols, glycerol, ethylenediamine, etc., or irradiation, to alter the properties of the oxidized cellulose.

The degradation of oxidized cellulose is through hydrolytic cleavage of the cellulose polymer and therefore, the oxidized material should be dehydrated following oxidation to minimize degradation prior to use. Thus, the dehydration process can have a significant effect on the mechanical and degradation properties of oxidized biocellulose. Indeed, the dehydration process therefore provides an additional means to control the mechanical and degradation properties of oxidized biocellulose depending on the requirements of the final application.

Air-drying or solvent dehydration followed by air-drying results in a material with low mechanical strength and decreased degradation properties. As described herein, air-drying refers to drying in ambient atmosphere at a temperature between about 20-50° C. As stated above, solvent dehydration involves a water-miscible solvent such as methanol, ethanol, propanol, isopropanol, acetone, and mixtures thereof. Supercritical $CO_2$ drying provides a biocellulose material that maintains much of its original strength and provides an open porous structure that demonstrates a higher rate of bioresorbability.

Many other variations and details of construction, composition and configuration will be apparent to those skilled in the art and such variations are contemplated within the broad scope of the present invention.

EXAMPLES

Example 1

Production of Microbial Cellulose by *Acetobacter xylinum*

This example describes the production of microbial cellulose by *Acetobacter xylinum* suitable for use in preparing oxidized cellulose.

Sterilized media was inoculated with *A. xylinum* from a propagation vessel prior to incubation. The media is based on a modified Schramm-Hestrin medium formulation as described in U.S. Ser. No. 10/132,171,. The inoculated media was used to fill bioreactor trays to a fixed volume, including, 50, 110, 220, 330, 360, and 440 g. These trays were covered with plastic sheeting and aeration ports are added for oxygen exposure during growth. Trays were then incubated under static conditions at a fixed temperature of 30° C. until optimal growth was achieved (4 days for 50 g to 21 days for 440 g).

Example 2

Processing of Microbial Cellulose

Microbial cellulose harvested from *A. xylinum* was chemically treated to remove bacterial by-products and residual media. But prior to chemical processing, the pellicles were first pressed with a pneumatic press to remove excess media.

The pressed cellulose pellicles were then chemically processed. The process entailed a dynamic soak in a 75° C. heated tank of 2-8% caustic solution containing sodium hydroxide for approximately one hour to depyrogenate. This chemical process was followed by a continuous rinse with filtered water to remove the caustic solution from the processed pellicles. Following the rinse, the pellicles were treated with 0.25% hydrogen peroxide at 40° C. for one hour to obtain a "whitened" appearance. Following chemical processing, the microbial cellulose films were again subject to a dehydration press in a pneumatic press to achieve the desired cellulose content and then subject to various post-chemical processing techniques.

Example 3

Oxidation of Microbial Cellulose

Chemically processed cellulose pellicles were oxidized. The cellulose samples were placed in a 0.1M $NaIO_4$ solution for either 4 or 24 hours at 40° C. Incubation was conducted in a closed reaction vessel within a darkened incubator to prevent side reactions of the cellulose. Following oxidation, the samples were rinsed to remove residual $NaIO_4$, punched to the desired size, packaged and sterilized using gamma irradiation for implantation.

Example 4 in vivo Degradation Study of Oxidized Microbial Cellulose

The in vivo investigation was conducted to evaluate the degradation behavior of the oxidized cellulose produced as described in Example 3, above.

Fifteen, female Sprague-Dawley rats were subject to ventral subcutaneous implantations in three locations with two test materials and one control in each animal. Cellulose that had been oxidized for 4 hours and 24 hours were used as the test materials and non-oxidized cellulose was used as the control.

Animals were sacrificed and explantation of all implants occurred at 2, 4 and 6 weeks following implantation with five animals at each time point. As expected, there was some fibrous attachment of the samples to the skin, muscle and other soft tissue at 2 weeks. At 4 and 6 weeks post implantation, essentially no gross fibrous response was noted in the peri-implant tissue.

Indications of degradation of the oxidized cellulose were evident as early as 4 weeks after implantation, as demonstrated in Table 1 and FIG. 1. Decreases in the size and weight of the oxidized samples compared to the controls over the 6 weeks indicate degradation occurring over time. The more highly oxidized sample (24 hr) displayed a more aggressive degradation pattern than the 4-hr oxidized samples, as expected.

The oxidized material demonstrated good biocompatibility upon implantation in the rat. In addition, implants engineered to degrade at different time points were shown to perform as expected.

TABLE 1

Mass of implants after sacrifice at 4 and 6 weeks

| Sacrifice Weeks | Non-oxidized Explant Wt - g | 4 hr oxidation Explant Wt - g | 24 hr oxidation Explant Wt - g |
|---|---|---|---|
| 4 | 0.12 ± 0.01 | 0.12 ± 0.15 | 0.09 ± 0.10 |
| 6 | 0.12 ± 0.01 | 0.08 ± 0.06 | 0.06 ± 0.01 |

Example 5

Effect of Periodate to Cellulose Ratio on the Oxidation of Microbial Cellulose with Sodium Meta-Periodate Solutions of $NaIO_4$ were prepared with varying periodate concentrations ranging from 6 to 25 mM. The oxidation solutions also contained 0.189M NaCl. Cellulose samples (2×4 cm strips) were weighed and then soaked in a 0.189M NaCl solution for 3 hours prior to incubation in periodate solution. Samples were incubated in periodate solutions with a range of $IO_4$:Cellulose ratios from 0.5 to 2. Incubation was conducted in closed reaction vessels within a darkened incubator (to prevent side reactions of the cellulose) for 17 hours at a temperature of 30±2° C. Following incubation samples were removed from the oxidizing solution and placed in an extract solution containing 35 mL of water for between 2-5 hours. Upon removal of the excess $NaIO_4$, the biocellulose samples were dried using one of three processes; supercritical drying (SCD), air-drying (AD), or solvent-exchange air-drying (SD). See Examples 9 and 10, below.

Figure 2:
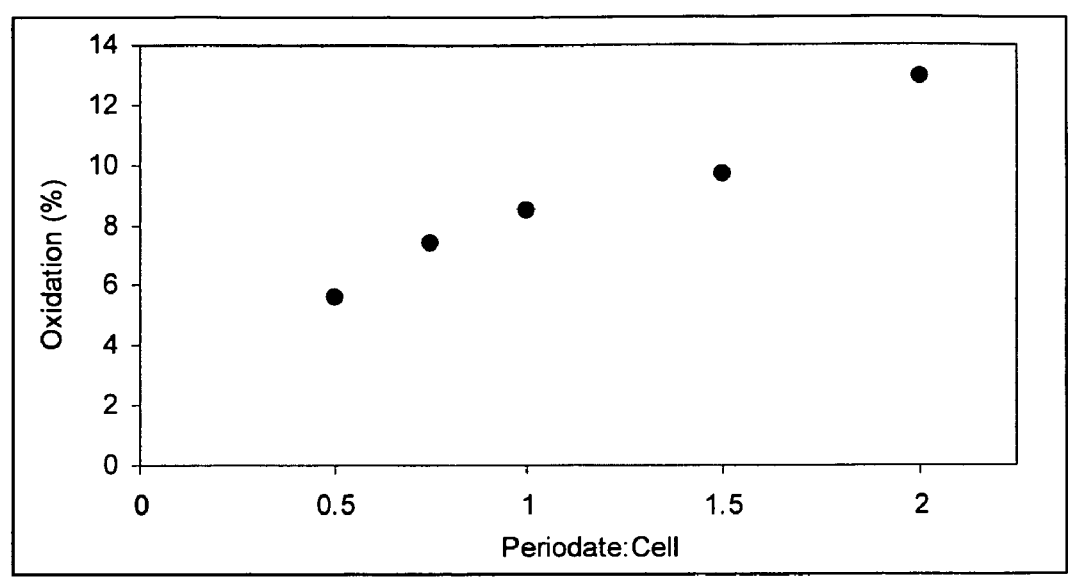
FIG. 2: Effect of Periodate:Cellulose Ratio on the Oxidation (%) of Biocellulose.

The level of oxidation was determined using UV/Vis analysis of the reaction and extract solutions by measuring the periodate absorbance at 290 nm. The moles of periodate from the reaction and extract solutions were subtracted from the moles of periodate in the initial reaction. The periodate oxidation occurred in a 1:1 ratio with the glucose repeat units in cellulose. Therefore, the number of repeat units oxidized and percent oxidation based on the dry weight of the biocellulose sample was calculated (FIG. 2).

Example 6

Effect of NaCl on the Oxidation and in vitro Degradation of Oxidized Microbial Cellulose Two sets of samples were made as described in Example 5 with a $IO_4$:Cellulose value of 0.75. One series was presoaked in 0.189M NaCl for six hours prior to oxidation in the presence of NaCl. The second series was soaked in water for six hours prior to oxidation in the absence of NaCl. Oxidation in the presence of NaCl resulted in an increased level of oxidation (Table 2) and differences in degradation properties.

The addition of a supporting electrolyte resulted in increased swelling of the cellulose polymer due to screening of the hydrogen bonding between polymer strands. Without wishing to be bound to any theory, it is believed that increased access to more oxidation sites results from the increased swelling allowing for a more homogeneous oxidation. Following oxidation the samples were dried with the SCD process.

An in vitro investigation was conducted to evaluate the degradation behavior of the oxidized cellulose produced as described above through the analysis of the degradation products and changes in mechanical strength. Samples were immersed in 25 mL of a buffered saline solution (8 g NaCl, 0.4 g KCl, 0.8 g $Na_2HPO_4$, 0.14 g $KH_2PO_4$, 1.0 g dextrose in 1.0 L water) with a pH of 7.4±0.2 and incubated at 37±2° C. Analysis was performed at 0, 1, 3, and 7 days. At each time point a small aliquot was analyzed by measuring the absorbance of the carbonyl absorbance at 232 nm. Mechanical strength was determined by measuring the suture pull-out force using a United tensile tester (Model SSTM 2KM) with Prolene 5.0 sutures.

Figure 3:
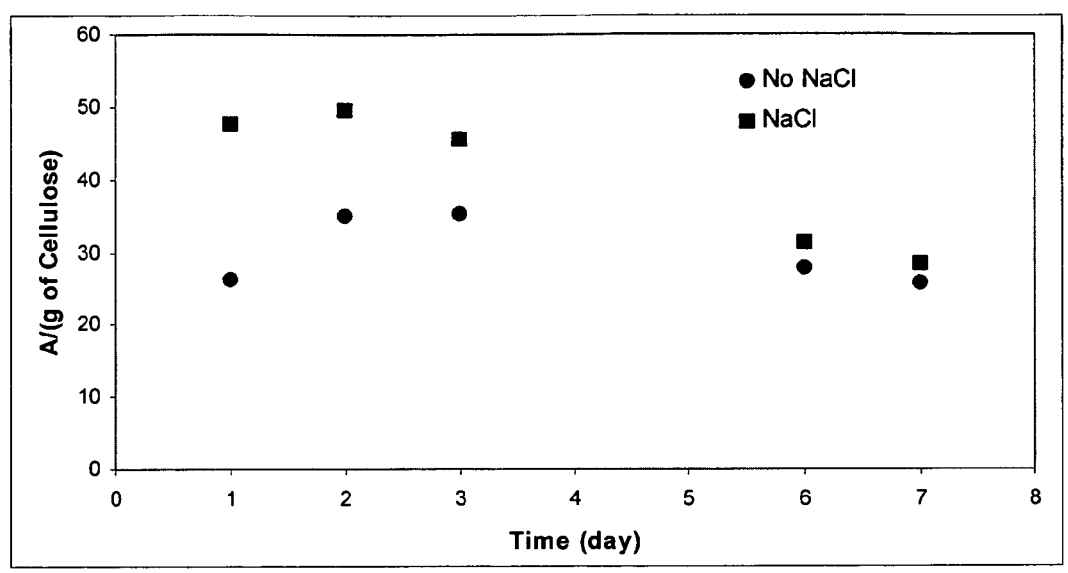
FIG. 3: Degradation product formation over the course of 7 days for biocellulose samples oxidized with and without NaCl in the oxidation solution. A/(g of cellulose) refers to the absorbance at 232 nm divided by the mass of cellulose (g) as determined by weighing the dried cellulose sample.

The addition of NaCl to the oxidation solution resulted in a material that was different from cellulose oxidized without NaCl. FIG. 3 demonstrates that the NaCl material had an increased rate of degradation as compared to oxidized material without NaCl, and Table 2 provides that while the initial strength of the material oxidized in the presence of NaCl was higher than without NaCl, over time the increased rate of degradation resulted in a similar reduction in suture pull-out strength.

TABLE 2

Oxidation and suture pull-out force values for biocellulose oxidized in the presence and absence of NaCl

| Sample | Oxidation (%) | Suture Pull-Out (Day 0) | Suture Pull-Out (Day 1) | Suture Pull-Out (Day 3) | Suture Pull-Out (Day 7) |
|---|---|---|---|---|---|
| Oxidation in the presence of NaCl | 13.0 ± 0.9 | 5.31 ± 0.44 | 1.45 ± 0.19 | 0.91 ± 0.08 | 0.73 ± 0.01 |
| Oxidation in the absence of NaCl | 9.2 ± 0.4 | 4.56 ± 0.05 | 2.07 ± 0.32 | 1.13 ± 0.06 | 0.9 ± 0.08 |

Example 7

Supercritical $CO_2$ Processing of Oxidized Microbial Cellulose

Following periodate oxidation according to the procedure in Example 5, samples were further processed using supercritical $CO_2$. Samples were subject to a series of exchanges in 100% methanol for a period of up to 48 hours. The cellulose was then wrapped in a polypropylene mesh and placed in a supercritical fluid exchange system (150 SFE System, Super Critical Fluid Technologies, Inc., Newark, Del.). Operating parameters for $CO_2$ (1500-1600 psi and 40° C.) were reached and maintained for an exchange time of between one and three hours. Following the cycle, the oxidized material was removed from the vessel in a dry form and weighed to determine the cellulose content. The dried samples underwent a degradation study as described in Example 5.

Figure 4:
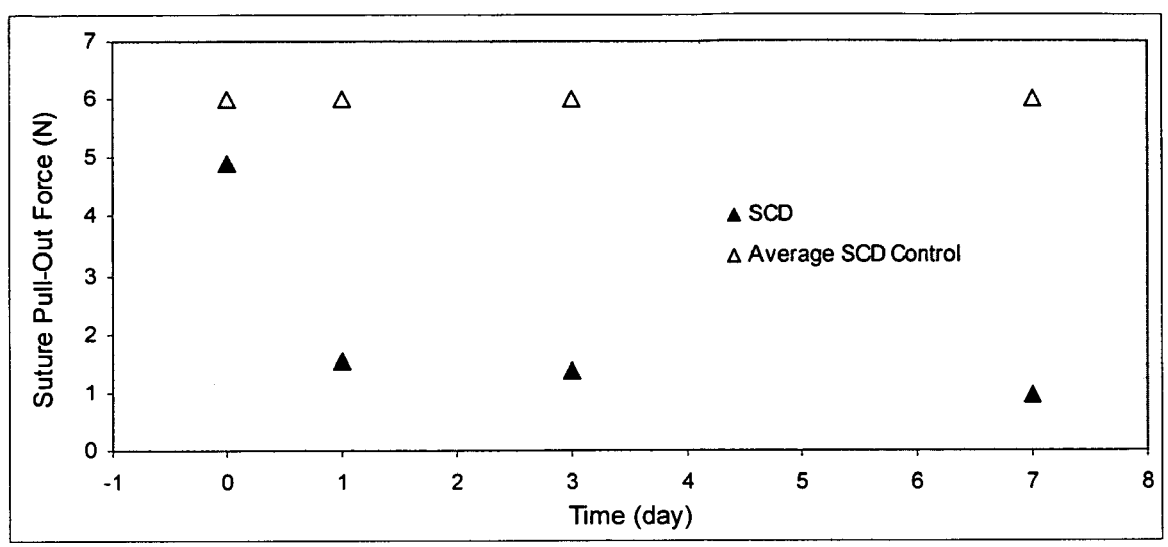
FIG. 4: Change in suture pull-out force over seven days for oxidized biocellulose following the SCD process.

FIG. 4 shows an approximate 18% decrease in strength due to the oxidation procedure in regards to the non-oxidized control sample (6.02±1.05 N). After one day of degradation the suture pull-out force is reduced to 1.53 N from 4.92 N and then slowly decreased to approximately 1 N over the next six days.

Example 8

X-Ray Diffraction of Oxidized Samples

SCD processing of oxidized biocellulose resulted in a material that maintained a high degree of crystallinity of the original non-oxidized material. As described in the Examples above, biocellulose samples were prepared to have levels of oxidation of 10 and 28%, and dried as described in this example.

Figure 5:
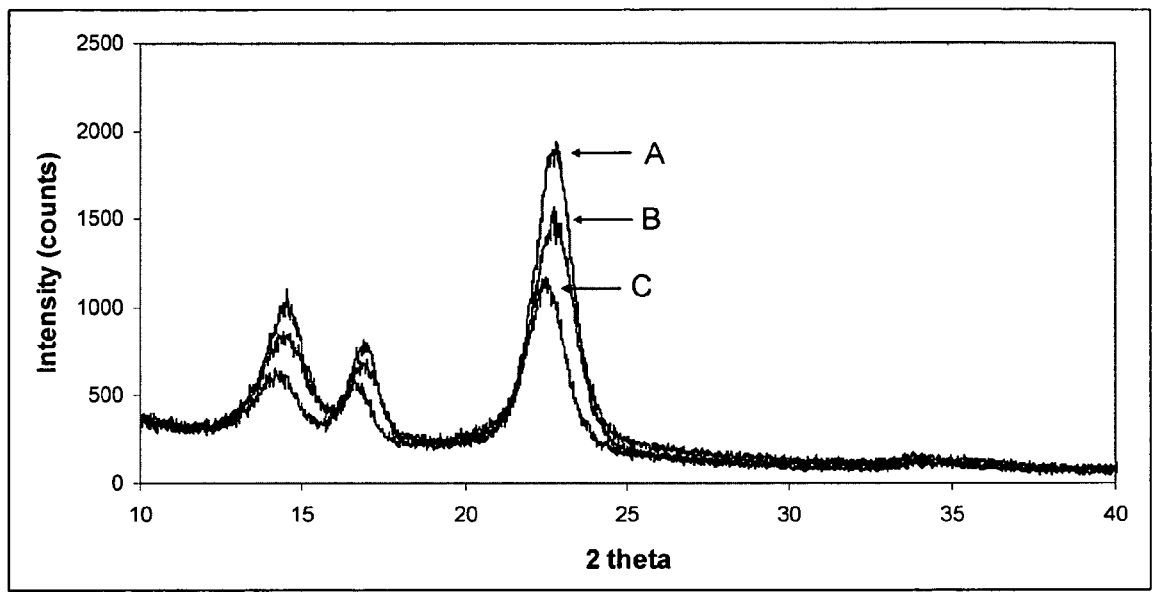
FIG. 5: X-ray diffractograms of non-oxidized (A), 10% oxidized (B), and 28% oxidized (C) biocellulose.

X-ray diffraction data was collected with a Rigaku Miniflex X-ray Diffractometer which produces X-rays by a 35 keV electron beam striking a Cu target. Data was collected from 5° to 60° 2θ. Data analysis was performed with JADE version 3.0 software. Diffractograms showed little change in crystal structure at 10 and 28% oxidation as compared to a non-oxidized sample (FIG. 5). The 2θ values show a small change in position upon higher oxidation indicating a shift in lattice spacing but the overall crystal structure remains the same. The preservation of the crystal structure upon oxidation contributed to the oxidized biocellulose maintaining mechanical strength following the oxidation and drying process.

Example 9

Air-Drying of Oxidized Microbial Cellulose

Following periodate oxidation according to the procedure in Example 5, samples were further processed using air-drying. The wet samples were placed between two pieces of polypropylene mesh and placed in a 37° C. incubator for between 18 and 36 hours. Following the drying procedure the samples were removed and weighed to determine the cellulose content. Table 3 shows the dramatic change in mechanical strength upon oxidation followed by air-drying as the strength decreases from 10 N (non-oxidized control) to 1.35 N at t=0. In addition, the strength shows a decrease of 70% compared to the oxidized SCD material at t=0.

TABLE 3

Suture pull-out values for oxidized microbial cellulose following various drying processes

| Drying Process | Day 0 (N) | Day 1 (N) | Day 3 (N) | Day 7 (N) |
|---|---|---|---|---|
| SCD | 4.92 ± 0.86 | 1.53 ± 0.32 | 1.38 ± 0.07 | 0.95 ± 0.04 |
| AD | 1.35 ± 0.44 | 1.28 ± 0.04 | 0.94 ± 0.28 | 1.07 ± 0.24 |
| SD | 1.32 ± 0.55 | 1.45 ± 0.21 | 0.95 ± 0.21 | 0.80 ± 0.05 |

Example 10

Solvent-Dehydration Followed by Air-Drying of Oxidized Microbial Cellulose

Following periodate oxidation according to the procedure in Example 5, samples were further processed using a solvent dehydration step followed by air-drying. Samples were subject to a series of exchanges in 100% methanol for a period of up to 48 hours. Rather than using SCD processing, following solvent exchange the samples were placed between two pieces of polypropylene mesh and placed in a 37° C. incubator for between 18 and 24 hours. Following the drying procedure the samples were removed and weighed to determine the cellulose content. As seen with the AD samples there is a dramatic decrease in mechanical strength upon oxidation as the SD samples show a decrease from 8.4 N (non-oxidized control) to 1.3 N following oxidation. Both AD and CD oxidized samples show similar suture pull-out values (Table 3) which suggests the resulting structure of the material is similar.

What is claimed is:

1. A method of making a bioresorbable oxidized biocellulose comprising (i) producing microbial cellulose, (ii) pre-soaking the biocellulose in an aqueous solution containing an electrolyte at a concentration is in the range of 0.001 M to 1.0 M for 30 minutes to 24 hours, and (iii) oxidizing the microbial cellulose with a solution of sodium meta-periodate in the presence of the solution of step (ii); wherein the electrolye is NaCl.

2. The method of claim 1, wherein the microbial cellulose is produced by *Acetobacter xylinum*.

3. The method of claim 1, wherein the desired degree of oxidation is achieved by varying a factor selected from the group consisting of periodate concentration, periodate solution volume, periodate:cellulose ratio, reaction temperature, reaction duration, and a combination thereof.

4. The method of claim 3 wherein the molarity of periodate ranges from 0.005M to 1.0M.

5. The method of claim 3 wherein the ratio of periodate to cellulose ranges from 0.05 to 10.

6. The method of claim 3 wherein the temperature is between 5° C. and 50° C.

7. The method of claim 3 wherein the oxidation of step (iii) is reacted for 30 minutes to 24 hours.

8. The method of claim 1, wherein the oxidized biocellulose is dried by a method selected from the group consisting of at least one of air-drying, oven drying, manually dehydration, solvent dehydration, drying over a desiccant, drying under vacuum, lyophilization, and supercritical fluid drying.

9. The method of claim 8 wherein the oxidized biocellulose is solvent dehydrated with acetone, methanol, ethanol, 1-propanol, iso-propanol, 1-butanol, 2-butanol, tetrahydrofuran, or glycerol.

10. The method of claim 8 wherein the oxidized biocellulose is solvent dehydrated with methanol or acetone followed by exchange with supercritical $CO_2$.

11. The method of claim 8 wherein the material is placed in a chamber at a temperature ranging from 20° C. to 100° C.

12. A method for making a bioresorbable medical material comprising (i) producing a microbial cellulose, (ii) pre-soaking the microbial cellulose in an aqueous solution containing NaCl in a concentration in the range of 0.001 M to 1.0 M for 30 minutes to 24 hours, and (iii) oxidizing the microbial cellulose with a solution of sodium meta-periodate in the presence of the solution of step (ii), whereby a bioresorbable medical material is made.

13. The method of claim 12, wherein the medical material is selected from the group consisting of sutures, hemostats, wound coverings, implantable tissue substitutes, tissue engineering matrices, or adhesion prevention devices.

14. The method of claim 12, wherein the medical material is used for repair and/or regeneration of a musculoskeletal tissue, a neurological tissue; cardiovascular tissue, abdominal tissue, bladder neck suspension, gastroplasty, hernia repair, gastrointestinal closure, guided tissue regeneration for a dental application, or a bulking agent for plastic or reconstructive surgery.

15. The method of claim 14, wherein the neurological tissue comprises dura.

16. The method of claim 1, wherein the biocellulose is pre-soaked for 3 hours.

17. The method of claim 1, wherein the biocellulose after the step of oxidizing has a suture pull-out strength of 5.31±0.44 N.

18. The method of claim 1, wherein the electrolyte concentration is in the Range of 0.1 to 0.5 M.

19. The method of claim 1, wherein the biocellulose is pre-soaked for 6 hours.

* * * * *